United States Patent [19]

Bannister

[11] Patent Number: 5,114,561
[45] Date of Patent: May 19, 1992

[54] OXYGEN PROBE ASSEMBLY

[75] Inventor: Michael J. Bannister, Glen Waverley, Australia

[73] Assignee: Commonwealth Scientific and Industrial Research Organization, Australia

[21] Appl. No.: 585,084
[22] PCT Filed: Mar. 21, 1989
[86] PCT No.: PCT/AU89/00113
§ 371 Date: Oct. 31, 1990
§ 102(e) Date: Oct. 31, 1990
[87] PCT Pub. No.: WO89/09398
PCT Pub. Date: Oct. 5, 1989
[51] Int. Cl.$^5$ .............................................. G01N 27/26
[52] U.S. Cl. .................................... 204/421; 204/424; 204/428
[58] Field of Search ........................ 204/421, 424, 428
[56] References Cited

U.S. PATENT DOCUMENTS

| | | | |
|---|---|---|---|
| 4,187,163 | 2/1980 | Steinke et al. | 204/428 |
| 4,193,857 | 3/1980 | Bannister et al. | 204/428 |
| 4,200,511 | 4/1980 | Sato et al. | 204/428 |
| 4,209,377 | 6/1980 | Shinohara et al. | 204/424 |
| 4,212,720 | 7/1980 | Maurer et al. | 204/424 |
| 4,253,302 | 3/1981 | Asano et al. | 204/428 |
| 4,789,454 | 12/1988 | Badwal et al. | 204/421 |
| 4,814,061 | 3/1989 | Blumenthal et al. | 204/428 |

*Primary Examiner*—John Niebling
*Assistant Examiner*—Bruce F. Bell
*Attorney, Agent, or Firm*—Sughrue, Mion, Zinn, Macpeak & Seas

[57] ABSTRACT

An oxygen probe assembly comprising an oxygen sensor (5) and means (8, 3) for directing a test gas and reference gas to the appropriate electrodes (7, 1) of the sensor, said assembly having associated therewith catalyst means (13, 6) arranged so that the test gas, the reference gas, or both said gases are separately contacted with the catalyst means before approaching the working surface(s) of the electrodes, whereby combustibles in the gases are oxidized; and/or means whereby the test gas, the reference gas, or both of said gases are conveyed to the said working surface(s) by way of a path (10, 4) which is of sufficient length to allow the said gas or gases to attain thermodynamic equilibrium at the probe temperature before coming into contact with the said working surface(s).

6 Claims, 4 Drawing Sheets

OXYGEN PROBE ASSEMBLY

This invention is concerned with oxygen probe assemblies which embody solid electrolyte sensors and are used to measure the oxygen potential of gases or molten metals. The invention is particularly concerned with probe assemblies capable of operating accurately at temperatures as low as 300° C.

Measurement of the oxygen potential of gases and molten metals using solid electrolyte sensors is well documented. For example, a sensor designed primarily for determinations in molten copper is described in Australian patent No. 466,251 and in the corresponding patents, U.S. Pat. No. 4,046,661, United Kingdom No. 1,347,937, Canadian No. 952,983, Belgian No. 782,180, Japanese No. 80 17340 and West German Offenlegungsschrift No. 22 18227.0. Modifications, particularly to the electrolyte, to improve the sensor for measurements in gases are described in Australian patent No. 513,552 and its equivalents U.S. Pat. No. 4,193,857, United Kingdom No. 1,575,766, Canadian No. 1,112,438, West German Offenlegungsschrift document No. 27 54522.8 and Japanese patent application No. 146208/77.

The solid electrolyte oxygen sensor uses the fact that when a solid membrane of a material with good oxygen ion conductivity and negligible electronic conductivity, termed a solid electrolyte, is held with its opposite faces in contact with materials having different oxygen potentials, an emf is established across the membrane. If one of the oxygen-containing materials is the gas or molten metal under investigation and the other is a reference material of known oxygen potential, then the emf (E) is given by the Nernst relationship:

$$E = \frac{RT}{nF} \cdot \ln\left(\frac{p_{O_2} \text{ (reference material)}}{p_{O_2} \text{ (test material)}}\right) \quad (1)$$

where:
LR = the gas constant,
T = the absolute temperature,
n = 4 (the number of electrons transferred per oxygen molecule),
F = the Faraday constant, and
$p_{O_2}$ = the oxygen partial pressure.

This emf is measured using electrodes, reversible to the $O_2/O^{2-}$ redox equilibrium, placed in electrical contact with the opposing faces of the solid electrolyte membrane.

Australian patent no.466,251 describes various geometrically distinct forms of solid electrolyte oxygen sensor. The most commonly-used form is that of a tube; either open-ended or closed at one end, made entirely from the solid electrolyte. Other designs use the solid electrolyte as a disc or pellet, sealed in one end of a metal or ceramic supporting tube. In all cases the reference environment, which is generally air, is maintained on one side of the tube (commonly on the inside) and the test environment is exposed to the other side of the tube.

Many solid electrolyte materials are known to be suitable for use in oxygen sensors. Examples include zirconia or hafnia, both fully stabilized or partially stabilized by doping with calcia, magnesia, yttria, scandia or one or a number of rare earth oxides and thoria, also doped with calcia, yttria or a suitable rare earth oxide. Australian patent 513,552 discloses the addition of alumina to these solid electrolyte materials to produce a composite solid electrolyte which is particularly suitable for sealing into the end of an alumina tube, thereby making a rugged and leak-tight sensor useful for demanding industrial applications. Australian patent application No.47828/78 and the corresponding patents or applications U.S. Pat. No. 4,240,891, United Kingdom application No. 79 19671, Canadian application No. 329,100, Japanese application No. 69529/79 and West German application No. 29 22947.8 disclose the use of magnesium aluminate spinel as an alternative to alumina, either for the supporting tube or as the inert diluent in the composite solid electrolyte material.

The electrodes on solid electrolyte oxygen sensors generally consist of porous coatings of noble metals such as platinum, gold, palladium or silver, or alloys of these elements. For measurements in gases using a gaseous reference, an electrode is required on each surface of the solid electrolyte; for measurements in molten metals an electrode is required only on the reference side of the solid electrolyte, and then only if a gaseous reference is used. If a solid reference, e.g., a metal/metal oxide mixture, is used there is no need for a separate noble metal electrode; the solid reference mixture serves as the electrode.

The electrodes participate in the exchange reaction between gaseous oxygen molecules and oxygen ions in the solid electrolyte by donating or accepting electrons. The overall equilibrium at each electrode is represented by the equation:

ti $O_2$ (gas) + 4$e$ (electrode) = 2 $O^{2-}$ (electrolyte) 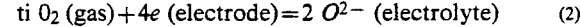 (2)

The electrodes may also help to catalyse this reaction. For example platinum, the most commonly used electrode material on solid electrolyte oxygen sensors, shows a high catalytic activity for this oxygen exchange reaction at elevated temperatures.

In the past, solid electrolyte oxygen sensors with noble metal electrodes have generally been used at temperatures above 600°-700° C. As operating temperature is reduced below 600° C., the following characteristics become increasingly evident:

(a) The total impedance rapidly increases, reaching megohm levels.
(b) The response time increases from a fraction of a second to many minutes.
(c) An emf appears when none is predicted (zero error).
(d) The emf is not ideal (i.e. it does not follow the Nernst equation) even after correction for zero error.
(e) The emf may depend on the gas flow rate.
(f) The emf under fuel-rich conditions (e.g. gas mixtures with high $CO/CO_2$ ratios) is very greatly in error.

The increased impedance may be at least partly counteracted by controlling the electrolyte composition, in particular its impurity content, to maximize its ionic conductivity, and by increasing the ratio electrode area/solid electrolyte membrane thickness of the sensor. Response time and emf accuracy at low temperatures may be enhanced by controlling the physical characteristics of the electrodes, i.e. porosity, particle size, layer thickness, etc. In general this means ensuring a very porous, extremely fine-grained texture in the electrodes. Noble metal electrodes, however, undergo morphology changes due to sintering and grain growth when exposed to higher temperatures, to the detriment of their subsequent low temperature performance.

In International Patent Application No. PCT/AU84/00013 (WO 84/03149) we described electrode materials for solid electrolyte oxygen sensors which enable such sensors to generate ideal (i.e. Nernstian) emfs under oxygen-excess gaseous conditions at temperatures substantially below those at which conventional noble metal electrodes begin to show non-ideal behaviour, and as low as 300° C.

These electrode materials are solid solutions in uranium dioxide of one or more other metal oxides with oxygen-metal atom ratios less than or equal to two, provided that at least one of said other metal oxides has an oxygen/metal atom ratio of less than two. Typical oxides useful as solutes in these uranium dioxide-based solid solution electrode materials are scandia ($Sc_2O_3$) and yttria ($Y_2O_3$); other oxides which dissolve in uranium dioxide, such as calcia (CaO) and the rare earth oxides, are also suitable. It is an object of the present invention to provide means whereby the performance of oxygen sensors especially at lower temperatures can be enhanced.

A further object is to provide improvements in oxygen probe assemblies which have the effect of reducing the importance of the electrode material, enabling sensors with conventional electrodes to give quite good behaviour at low temperatures. The improvements also seek to provide better low temperature performance with assemblies incorporating the advanced electrode materials described in our earlier application (WO 84/03149).

The present invention arises from our observation that emf errors in oxygen sensors operating at 300°-500° C. result predominantly from the presence of low levels of combustible species in the gases exposed to the sensor. It is well known that carbon monoxide, which displaces oxygen from adsorption sites on the electrode at such temperatures, is a source of emf error. We have also found that other species such as methane and propane have a qualitatively similar effect. Low levels of unburnt combustibles are common in boiler flue gases, one of the important applications for oxygen sensors. We have also found that most sources of reference air for the sensors also contain combustibles which cause errors at the reference electrode.

To prevent these combustibles from influencing the sensor emf, it is necessary to ensure that they are removed before they reach the electrodes on the sensor. If the sensor is operated at high temperatures, e.g. 700° C. or above, such removal occurs by reaction of the combustibles with oxygen in the reference air or with the oxygen which is normally in excess in the boiler flue gases. When the sensor is operated at lower temperatures the oxidation process does not bring about complete removal of combustibles in the case of conventional probe assemblies.

One approach to this problem is to oxidise the combustibles over a suitable catalyst external to the oxygen probe and we have found that errors in emf are reduced by passing the gases over a heated platinum catalyst before they reach the inner and outer electrodes of the sensor.

Such an arrangement, however, would be generally unsuitable for commercial operations and accordingly we have developed a modified form of oxygen probe which enables a suitable catalyst to be incorporated therein.

Thus, in accordance with one aspect of the present invention, there is provided an oxygen probe assembly comprising an oxygen sensor and means for directing a test gas and reference gas to the appropriate electrodes of the sensor, said assembly having associated therewith catalyst means arranged so that the test gas, the reference gas, or both gases are separately contacted with the catalyst means before approaching the working surface(s) of the electrodes, whereby combustibles in the gases are oxidized.

Our investigations have also shown that the use of a catalyst may not be essential if the reference and/or test gases are held at the probe temperature for sufficient time to allow the gases to attain thermodynamic equilibrium at that temperature. This can be achieved by allowing the gases to diffuse to the electrode along a path of sufficient length for equilibrium to be attained. Such a path may take the form of a narrow labyrinth or annulus through which the gases must diffuse before reaching the electrode. We have termed such a labyrinth or annulus a "diffusion space".

Preferably the probe assembly includes both the catalyst and the diffusion space. Preferably also, the catalyst material is coated on at least part of the wall(s) defining the diffusion space(s)

The above and other aspects of the invention are further described and illustrated by the following description, which relates to one preferred (and non-limiting) embodiment of the invention. Reference will be made to the accompanying drawings, in which.

Figure 1:
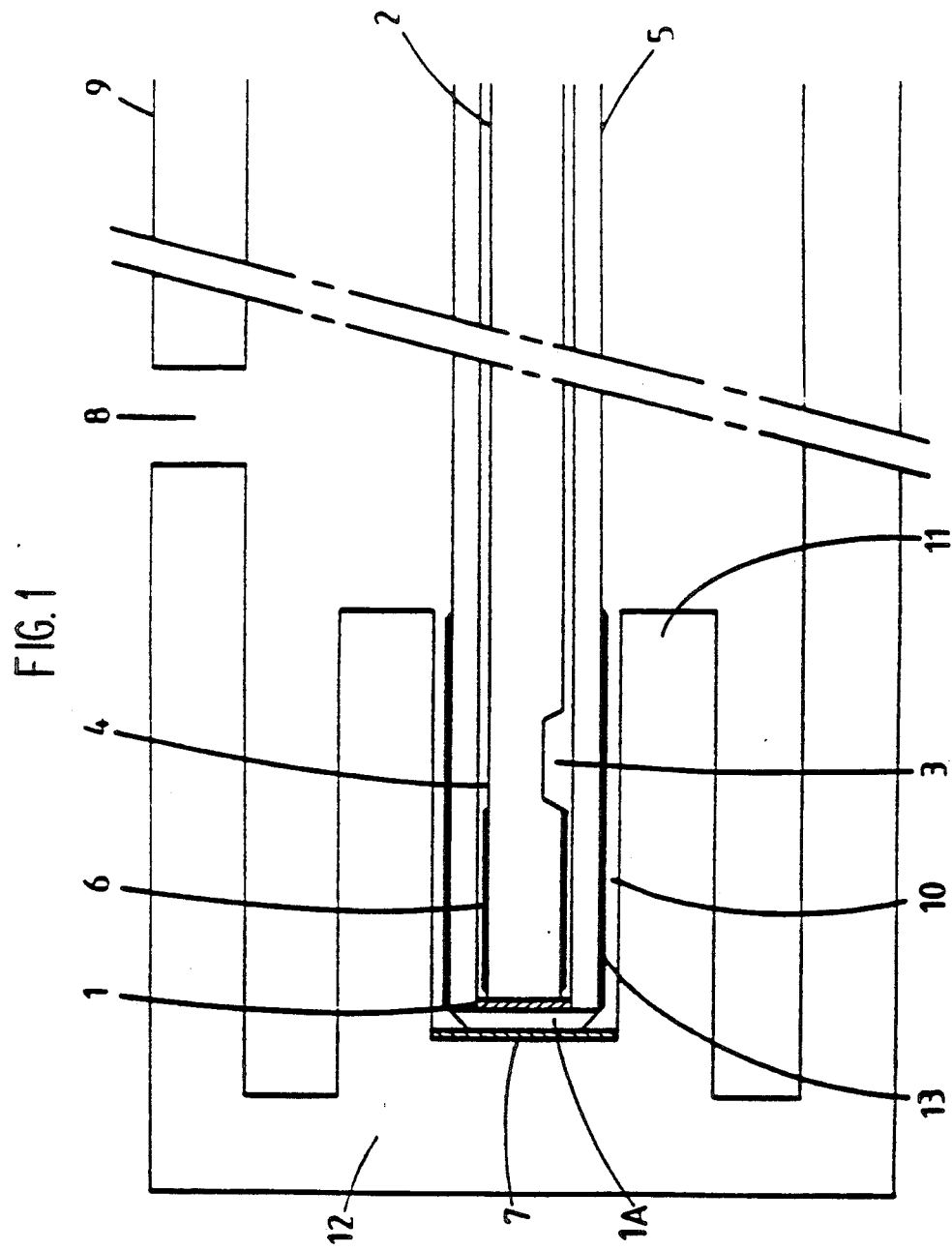
FIG. 1 is a diagrammatic cross-section of a probe constructed in accordance with the invention.

In the modified oxygen probe assembly of FIG. 1, the oxygen sensor comprises a solid electrolyte disk (1A) which is mounted at the end of a ceramic tube 5 (the "sensor tube"). The electrolyte disk 1A has porous electrode 1 on its inner surface. Catalytic oxidation of combustibles is achieved within the assembly. Instead of impingeing directly on the inner electrode 1, reference air is introduced via an inner tube 2 and emerges from one or more apertures 3 located typically 1-2 cm from the electrode 1. Impurities in the air can only affect the sensor emf by diffusing from aperture(s) 3 to inner electrode 1 through the annular space 4 between tubes 2 and 5. In this region, the outer wall of tube 2 and, optionally, the inner wall of sensor tube 5 have a coating 6 of a suitable catalyst e.g. porous platinum. Combustibles in the air are removed by oxidation at the catalyst surface before they diffuse to the electrode 1.

The same principle is used to clean the test gases before they reach the outer electrode 7, which is in contact with the electrolyte disc 1A. The gases approach the electrode through one or more holes 8 in metal sheath 9 which protects the sensor 5 and provides the electrical connection to the outer electrode 7, which is supported on the base 12 of sheath 9. To reach the electrode they must then diffuse along the annular space 10 between sensor tube 5 and a sleeve 11 which forms part of the base 12 of the sheath 9. The outer wall of sensor tube 5 and, optionally, the inner wall of sleeve 11 are coated with catalyst 13, for example porous platinum. Combustibles in the external gas are removed by oxidation at the catalyst surface as they diffuse towards outer electrode 7 along annular space 10. The best low temperature behaviour is obtained if catalyst layers 6 and 13 are both present; however, the presence of diffusion spaces 4 and 10 without catalyst also gives significant improvements in performance.

Typical dimensions for the elements described above are as follows:

| | |
|---|---|
| Inner tube (2) | 3.5-4 mm o/d |
| Sensor tube (5) | 8 mm o/d; 5 mm i/d |
| Sleeve (11) | 9-10 mm i/d; length 25 mm |
| Inner Annulus (4) | 1-1.5 mm wide; |
| Outer Annulus (10) | 1-2 mm wide; depth 25 mm. |

These dimensions are given by way of example only.

Figure 2:
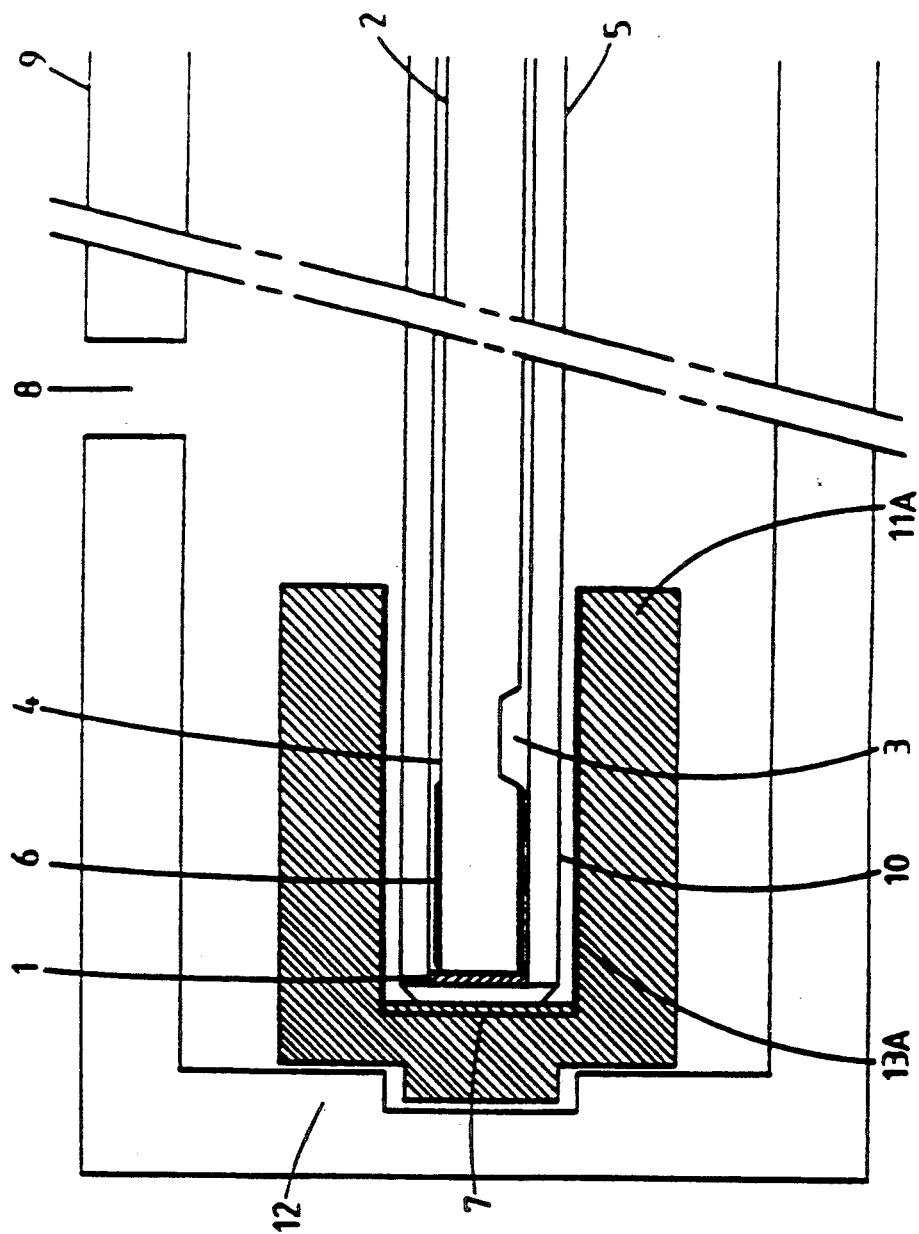
FIG. 2 is a modified construction of the probe of FIG. 1.

In the probe of FIG. 2, the integral sleeve 11 is replaced by a separately formed and attached sleeve 11A and the catalyst 13A is coated on the inner wall of the sleeve.

The following examples further illustrate the invention.

EXAMPLE 1

The following tests were carried out to demonstrate that combustible contaminants cause errors in the signals developed by solid electrolyte oxygen sensors at low temperatures, and that these errors can be eliminated by catalytic oxidation of the contaminants.

A ceramic oxygen sensor comprising a zirconia-scandia-alumina disc welded to the end of an alumina tube, carrying porous electrodes which were a mixture of platinum metal and a solid solution of urania ($UO_2$) and scandia ($Sc_2O_3$), was held in a furnace with its outer electrode exposed to flowing oxygen and its inner electrode exposed to flowing air. A system of flow meters and flow control valves was used to introduce controlled quantities of various gases (carbon monoxide, methane, natural gas and liquified petroleum gas) into the air stream. Two experiments were performed with the sensor temperature at 427° C.

a) The concentration of combustible contaminant was varied and the effect on the sensor signal was recorded.

b) For a fixed level of each combustible contaminant, the effect was observed of passing the air/combustible mixture over an oxidation catalyst, whose temperature was regulated, before sending it to the sensor.

Figure 3:
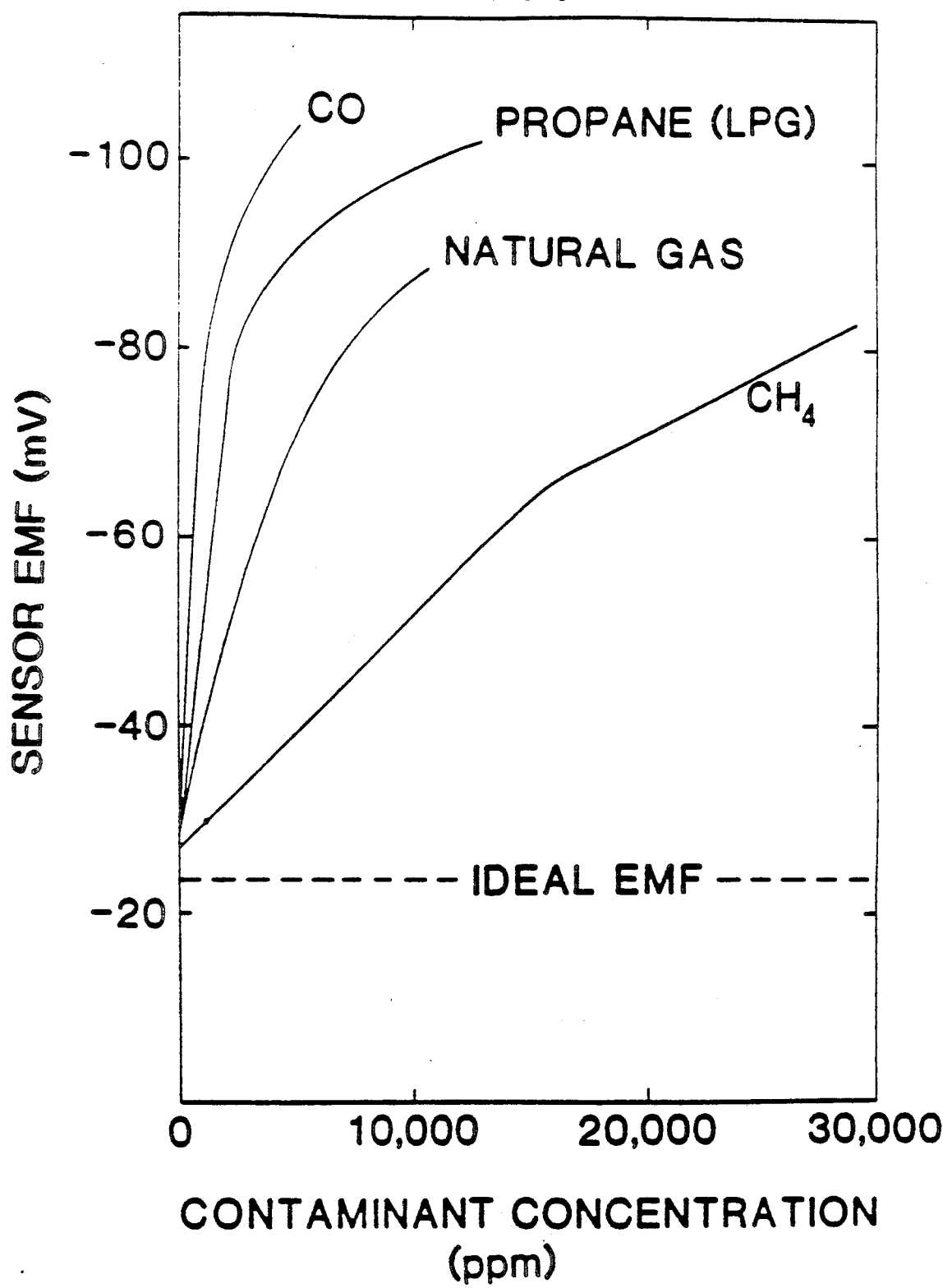
FIG. 3 is a graph showing the effects of combustible contaminants on sensor emf.

All the combustible species influenced the emf developed by the sensor (FIG. 3). The changes in signal, which depended on the nature of the contaminant and the concentration introduced, were considerably greater than would he expected simply on the basis of their influence on the residual oxygen concentration in the air stream, assuming complete combustion. The results suggest that the combustible molecules successfully displaced oxygen from adsorption sites on the sensor electrode, creating a surface condition typical of that expected for low oxygen partial pressure conditions.

Figure 4:
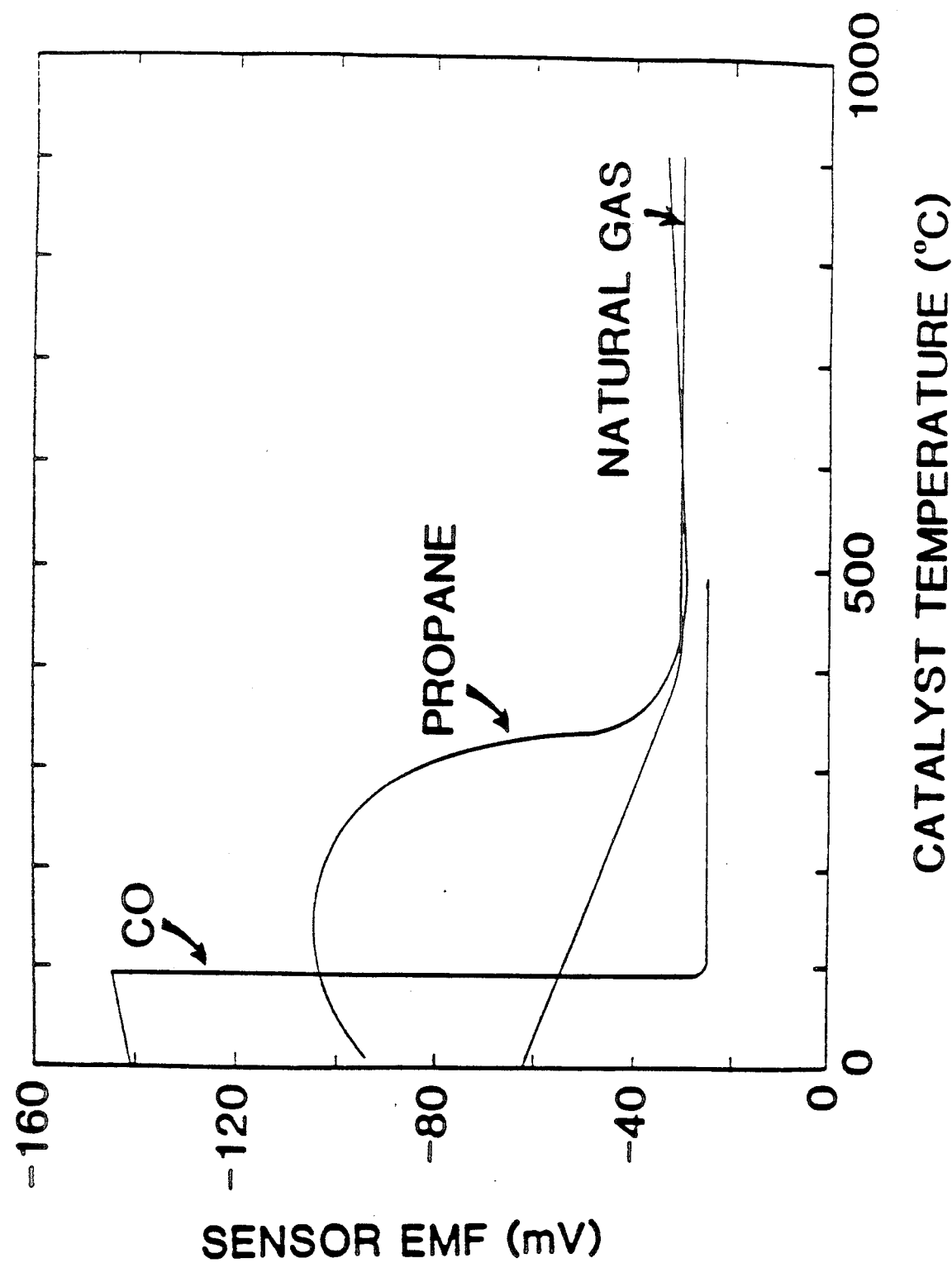
FIG. 4 is a graph showing how such emf errors are eliminated by passing the combustible-containing gases over an oxidation catalyst.

These emf errors were eliminated by passing the combustible/air mixture over a heated oxidation catalyst (in this case, an automotive exhaust catalyst comprising platinum-group metals dispersed on a ceramic substrate) before it reached the sensor (FIG. 4). The catalyst temperature required to ensure complete elimination of the error depended on the nature of the combustible contaminant, being lowest ($\sim 100°$ C.) for CO and higher (400°-500° C.) for propane and natural gas. The mechanism of removal is presumed to involve catalytically-assisted combustion of the contaminants to form molecular species ($CO_2$, $H_2O$) which do not influence the emf developed by the sensor.

EXAMPLE 2

The following tests were performed to demonstrate that it is possible to greatly reduce the influence of combustible contaminants on the emf of an oxygen sensor operated at low temperatures, by providing a stagnant diffusion zone and an internal oxidation catalyst region in the manner outlined in FIG. 1.

Two sensors of the type described in Example 1 were used in these experiments. Both carried electrodes of porous platinum (Platinum Paste No.6082, Engelhard Industries Pty. Ltd.); for sensor No.1 the electrodes were baked on at 600° C., and for sensor No.2 the electrodes were fired at 1000° C. The higher firing temperature yields an electrode with coarser microstructure and lower electrochemical activity.

The sensors were held simultaneously in a furnace with their outer electrodes exposed to flowing air. A cylindrical plug of automotive oxidation catalyst was located in the hot zone of the furnace to remove combustible impurities from the air. Contact to the outer electrodes was made using platinum wires.

Two different internal contact arrangements were alternated between the two sensors. The first (contact A) comprised a twin-bore alumina tube with a platinum wire in one bore, the wire ending in a flat spiral which made contact to the inner electrode of the sensor. The two bores were also used to carry a test gas which impinged directly on the inner electrode. The second contact (B) differed from contact A in two important respects. Openings were cut intersecting each bore about 10 mm from the contact end of the alumina tube, so that the test gas emerged via the openings and did not impinge directly on the inner electrode. Additionally, the wall of the twin-bore tube from the gas exit openings to the contact end was coated with porous platinum (Platinum Paste No.6082, Engelhard Industries Pty. Ltd.) baked on at 600° C. The platinum coating served as an oxidation catalyst to remove combustible contaminants from the test gas as it diffused towards the inner electrode from the gas exit openings.

Four different test gases were used inside the sensors, i.e. oxygen, air, 1.5% oxygen in nitrogen and 0.36% or 0.114% oxygen in nitrogen. Tests were carried out between 300° and 600° C. Every possible combination of temperature, sensor, internal contact and test gas was investigated. Each test condition was monitored continuously and held for 24 hrs. to ensure that equilibrium had been attained.

Results are presented in Table 1, in which the observed sensor emfs are compared against the theoretical values calculated using the Nernst equation. In general at 400° C. and below contact B gave errors which were considerably less than contact A. Except for the results with sensor 1 and 0.36% $O_2$ in $N_2$, which suggest that the gas flow rate in that experiment was not high enough to prevent contamination of the test gas by atmospheric oxygen, contact B gave emfs accurate to 1 mV down to 400° C. and in most cases down to 350° C. On the other hand contact A began to show significant errors at 400° C., and very large errors indeed at 350° and 300° C. The signs of the errors (inner electrode too negative) were consistent with the effect of combustible contaminants reported in Example 1. The tendency for the error to become worse with a decrease in the oxygen concentration of the test gas is as expected if the error is related to the presence of an oxidizable contaminant. Thus these results are best explained by trace levels of combustibles in the test gases which, particularly in the case of contact A, influenced the signals of both sensors at low temperatures. The experiment shows that the provision of an internal catalyst and the modification in gas path geometry incorporated in contact B substantially reduced the errors and lowered the minimum operating temperature of each sensor.

internal multibore contact tube, respectively, and baked on at 600° C.

The probe was mounted in a laboratory furnace and held at temperatures between 300° and 500° C. A gas mixing pump was used to supply various oxygen/nitrogen mixtures to the outer electrode, and also to add to the test gas mixtures 1 percent of a 95 volume percent $CO_2$ 5 P volume percent CO gas mixture, thus introducing 495 ppm of CO into the gas stream. Air was supplied to the inner electrode via the multibore contact tube. The probe temperature and sensor emf were recorded continuously and each test condition was maintained for 24 hrs. to ensure that equilibrium had been reached.

The purpose of the experiment was to establish the absolute accuracy of the probe over a range of oxygen concentrations (2 to 10 percent by volume) typical of air-excess combustion conditions, and to test whether

TABLE 1

Accuracy of Sensor Emfs

| Temperature (°C.) | Contact A | | | Contact B | | |
|---|---|---|---|---|---|---|
| | Sensor | % $O_2$ in gas | E(obs)-E(theor)(mV) | Sensor | % $O_2$ in gas | E(obs.)-E(theor)(mV) |
| 604 | 1 | 100 | 0.1 | 2 | 20.95 | 0.2 |
| 509 | 1 | 100 | 0.1 | 2 | 20.95 | 0.2 |
| 402 | 1 | 100 | −1.1 | 2 | 20.95 | 0.5 |
| 355 | 1 | 100 | −6.8 | 2 | 20.95 | 0.8 |
| 299 | 1 | 100 | −31.8 | 2 | 20.95 | 3.1 |
| 604 | 1 | 20.95 | 0.2 | 2 | 100 | 0.3 |
| 507 | 1 | 20.95 | 0.2 | 2 | 100 | 0.1 |
| 400 | 1 | 20.95 | −1.0 | 2 | 100 | −0.3 |
| 350 | 1 | 20.95 | −6.5 | 2 | 100 | −0.4 |
| 280 | 1 | 20.95 | −32.0 | 2 | 100 | 1.9 |
| 600 | 2 | 20.95 | −0.1 | 1 | 100 | 0.5 |
| 504 | 2 | 20.95 | −0.1 | 1 | 100 | 0.5 |
| 404 | 2 | 20.95 | −3.6 | 1 | 100 | −0.2 |
| 348 | 2 | 20.95 | −16.4 | 1 | 100 | 0.6 |
| 297 | 2 | 20.95 | −59.0 | 1 | 100 | 8.3 |
| 601 | 2 | 100 | 0.0 | 1 | 20.95 | 0.5 |
| 513 | 2 | 100 | −0.1 | 1 | 20.95 | 0.4 |
| 401 | 2 | 100 | −1.9 | 1 | 20.95 | −0.3 |
| 349 | 2 | 100 | −8.7 | 1 | 20.95 | 0.9 |
| 310 | 2 | 100 | −24.9 | 1 | 20.95 | −3.3 |
| 604 | 2 | 1.50 | 1.9 | 1 | 0.36 | 4.8 |
| 508 | 2 | 1.50 | 0.6 | 1 | 0.36 | 4.3 |
| 403 | 2 | 1.50 | −5.7 | 1 | 0.36 | 3.5 |
| 347 | 2 | 1.50 | −72.8 | 1 | 0.36 | −2.9 |
| 301 | 2 | 1.50 | −117.4 | 1 | 0.36 | −25.1 |
| 601 | 2 | 0.36 | 0.7 | 1 | 1.50 | 0.7 |
| 507 | 2 | 0.36 | 0.8 | 1 | 1.50 | 0.6 |
| 403 | 2 | 0.36 | −15.6 | 1 | 1.50 | 0.2 |
| 353 | 2 | 0.36 | −66.4 | 1 | 1.50 | −3.1 |
| 291 | 2 | 0.36 | −138.6 | 1 | 1.50 | −36.6 |
| 608 | 1 | 0.114 | 0.2 | 2 | 1.50 | 0.1 |
| 510 | 1 | 0.114 | 0.3 | 2 | 1.50 | 0.1 |
| 408 | 1 | 0.114 | −12.7 | 2 | 1.50 | 0.2 |
| 350 | 1 | 0.114 | −97.2 | 2 | 1.50 | 0.0 |
| 295 | 1 | 0.114 | −165.0 | 2 | 1.50 | −1.6 |
| 607 | 1 | 1.50 | 1.1 | 2 | 0.114 | −0.5 |
| 509 | 1 | 1.50 | 1.1 | 2 | 0.114 | −0.5 |
| 409 | 1 | 1.50 | −2.8 | 2 | 0.114 | 0.0 |
| 338 | 1 | 1.50 | −68.0 | 2 | 0.114 | −0.3 |
| 301 | 1 | 1.50 | −121.1 | 2 | 0.114 | −3.2 |

Theoretical values of E calculated using the equation:
E(theor,mV) = $4.960 \times 10^{-2}$ (T + 273.2)$\log_{10}$ (x/20.95) where x is the % $O_2$ in the test gas
T (°C.) is the experimental temperature

EXAMPLE 3

Tests were carried out on a complete oxygen probe assembly similar to that shown in FIG. 1. The sensor body and sensor electrodes were as described in Example 1, and the catalytic surfaces incorporated in the assembly comprised coatings of platinum paste (No.6082, Engelhard Industries Pty.Ltd.) applied to the outer wall of the sensor tube and the outer surface of the that accuracy was affected by the presence of a typical level of unburnt combustible (here, CO). After these tests the probe was heated to 900° C. in air and held for 4 hrs, then returned to the range 300° to 500° C. and retested. The purpose of this test was to evaluate whether the accuracy of the probe was affected by exposure to a temperature well above its anticipated temperature of application.

Results are given in Table 2. The small negative em error at 400° C. and above (1 to 2 mV) is almost certainly due to a slight temperature gradient across the sensor in the small laboratory furnace. This constitutes a "zero error" which may be subtracted from all the results. With this correction, the observed emfs are accurate to 1 mV down to 350° C. for oxygen concentrations from 2% to 21%. The accuracy was not influenced by the presence of 495 ppm of CO, or by heating the probe at 900° C. for 4 hrs. This example shows that a probe made according to the invention is capable of accurate performance down to relatively low temperatures, is tolerant of the presence of low levels of combustibles, and is able to withstand temperatures well above its normal operating temperature without degradation.

TABLE 2

Accuracy of Probe Emfs.

| Probe Condition | Temperature (°C.) | % O$_2$ | ppm CO | E(obs.)- E(theor)(mV) |
|---|---|---|---|---|
| As assembled | 476 | 20.95 | 0 | −1.1 |
| " | 394 | 20.95 | 0 | −1.2 |
| " | 354 | 20.95 | 0 | +0.3 |
| " | 304 | 20.95 | 0 | +3.0 |
| " | 502 | 100 | 0 | −1.1 |
| " | 399 | 100 | 0 | +0.3 |
| " | 354 | 100 | 0 | +1.5 |
| " | 304 | 100 | 0 | −49.6 |
| " | 502 | 2.095 | 0 | −1.5 |
| " | 503 | 2.074 | 495 | −1.4 |
| " | 400 | 2.095 | 0 | −0.7 |
| " | 399 | 2.074 | 495 | −0.7 |
| " | 350 | 2.095 | 0 | 0.0 |
| " | 350 | 2.074 | 495 | −0.1 |
| " | 299 | 2.095 | 0 | −3.7 |
| " | 300 | 2.074 | 495 | −3.3 |
| " | 501 | 4.19 | 0 | −1.4 |
| " | 502 | 4.149 | 495 | −1.3 |
| " | 398 | 4.19 | 0 | −1.1 |
| " | 398 | 4.149 | 495 | −0.8 |
| " | 348 | 4.19 | 0 | −1.0 |
| " | 349 | 4.149 | 4.95 | −0.9 |
| " | 299 | 4.19 | 0 | +1.9 |
| " | 298 | 4.149 | 495 | +1.9 |
| " | 502 | 10.475 | 0 | −1.3 |
| " | 502 | 10.371 | 495 | −1.3 |
| " | 399 | 10.475 | 0 | −0.9 |
| " | 400 | 10.371 | 495 | −0.8 |
| " | 350 | 10.475 | 0 | −1.2 |
| " | 350 | 10.371 | 495 | −0.5 |
| " | 299 | 10.475 | 0 | −4.7 |
| " | 299 | 10.371 | 495 | −3.5 |
| 900° C. 4 hrs. | 400 | 20.95 | 0 | −1.3 |
| " | 351 | 20.95 | 0 | −1.3 |
| " | 302 | 20.95 | 0 | −1.9 |
| " | 501 | 2.095 | 0 | −0.9 |
| " | 501 | 2.074 | 495 | −0.9 |
| " | 399 | 2.095 | 0 | −1.2 |
| " | 399 | 2.074 | 495 | −1.1 |
| " | 351 | 2.095 | 0 | −1.7 |
| " | 351 | 2.074 | 495 | −1.7 |
| " | 302 | 2.095 | 0 | −4.0 |
| " | 301 | 2.074 | 495 | −3.1 |
| " | 503 | 4.19 | 0 | −1.0 |
| " | 502 | 4.149 | 495 | −0.9 |
| " | 400 | 4.19 | 0 | −1.3 |
| " | 401 | 4.149 | 495 | −1.2 |
| " | 351 | 4.19 | 09 | −1.1 |
| " | 351 | 4.149 | 495 | −1.1 |
| " | 301 | 4.19 | 0 | −1.3 |
| " | 302 | 4.149 | 495 | −1.6 |

Theoretical values of E calculated as described below Table 1.

I claim:

1. An oxygen probe assembly comprising a solid electrolyte oxygen sensor and means for conveying a test gas and a reference gas to the appropriate electrodes of the sensor, characterized in that the means for conveying the test gas, the reference gas, or both of said gasses to the appropriate electrode(s) include a pathway in the form of a labyrinth or annulus which extends to the electrode and through which the gas must diffuse before reaching the electrode, and wherein at least part of the said labyrinth or annulus is coated with an oxidation catalyst, whereby combustible substances in the gas(es) passing through said pathway(s) are removed by catalytic oxidation over said catalyst before the gas(es) reach the appropriate electrode(s).

2. An oxygen probe assembly as claimed in claim 1, wherein the oxygen sensor comprises a solid electrolyte disk or pellet which is mounted at the end of a tube (the "sensor tube"), the electrolyte disk or pellet having or being in electrical contact with an electrode on each of its inner and outer faces; characterized in that at least the electrode end portion of the sensor tube is surrounded by an outer tube which, together with the sensor tube, defines a first annular space surrounding the sensor, whereby one of test or reference gases can enter the outer tube and diffuse through the first annular space to the outer electrode surface; and the sensor tube houses an inner tube which, together with the sensor tube, defines a second annular space within the sensor tube; said inner tube being provided with gas inlet and outlet means whereby the other of said gases can enter the second annular space and diffuse to the inner electrode surface, and at least one wall of the tubes which define the first and second annular space wholly or partly is coated with the oxidation catalyst.

3. An oxygen probe assembly as claimed in claim 1, wherein the oxygen sensor comprises a solid electrolyte disk or pellet which is mounted at the end of a tube (the "sensor tube"), the electrolyte disk or pellet having or being in electrical contact with an electrode on each of its inner and outer faces; characterized in that at least the electrode end portion of the sensor tube is surrounded by an outer tube which, together with the sensor tube, defines a first annular space surrounding the sensor, whereby the test gas can enter the outer tube and diffuse through the first annular space to the outer electrode surface; and the sensor tube houses an inner tube which, together with the sensor tube, defines a second annular space within the sensor tube; said inner tube being provided with gas inlet and outlet means whereby the reference gas can enter the second annular space and diffuse to the inner electrode surface, and at least one wall of the rubes which define the first and second annular space wholly or partly is coated with the oxidation catalyst.

4. An oxygen probe assembly as claimed in claim 2, characterized in that the sensor is housed within a tubular sheath having a closed end which carries an inwardly-directed cup or sleeve, the walls of which comprise the said outer tube, the sheath being provided with one or more gas inlet apertures.

5. An oxygen probe assembly as claimed in claim 4, characterized in that the cup or sleeve forms an integral part of the closed end of the sheath.

6. An oxygen probe assembly as claimed in claim 4, characterized in that the cup or sleeve is formed separately and attached to the closed end of the sheath.

* * * * *

UNITED STATES PATENT AND TRADEMARK OFFICE
CERTIFICATE OF CORRECTION

PATENT NO. : 5,114,561

DATED : May 19, 1992

INVENTOR(S) : Michael J. BANNISTER

It is certified that error appears in the above-identified patent and that said Letters Patent is hereby corrected as shown below:

On title page,
    item [73], line 2, change "Organization" to
        -- Organisation --

Signed and Sealed this

Fourteenth Day of September, 1993

Attest:

BRUCE LEHMAN

Attesting Officer      Commissioner of Patents and Trademarks